United States Patent

Looney et al.

[11] Patent Number: 6,152,874
[45] Date of Patent: Nov. 28, 2000

[54] ADJUSTABLE MULTI-PURPOSE CORONARY STABILIZING RETRACTOR

[75] Inventors: Christopher S. Looney, Roswell, Ga.; Gregory R. Furnish, Louisville, Ky.; Michael W. Hipps, Roswell, Ga.

[73] Assignee: Genzyme Corporation, Cambridge, Mass.

[21] Appl. No.: 08/936,414

[22] Filed: Sep. 25, 1997

Related U.S. Application Data

[63] Continuation-in-part of application No. 08/639,214, Apr. 26, 1996.
[60] Provisional application No. 60/026,905, Sep. 26, 1996.
[51] Int. Cl.⁷ ................................... A61B 1/313
[52] U.S. Cl. .......................... 600/214; 600/222
[58] Field of Search ..................... 600/121, 201, 600/203, 210, 213, 214–216, 217, 226–229, 234, 235, 240, 204, 219, 222

[56] References Cited

U.S. PATENT DOCUMENTS

| | | | |
|---|---|---|---|
| 2,693,795 | 11/1954 | Grieshaber | 600/213 |
| 2,863,444 | 12/1958 | Winsten | 600/214 |
| 3,409,013 | 11/1968 | Berry | 600/201 X |
| 3,503,398 | 3/1970 | Fogarty et al. | 600/210 |
| 3,729,006 | 4/1973 | Wilder et al. | 600/210 |
| 3,750,652 | 8/1973 | Sherwin | 600/219 X |
| 3,882,855 | 5/1975 | Schulte et al. | 600/201 X |
| 3,943,592 | 3/1976 | Bhaskar et al. | 600/240 X |
| 4,052,980 | 10/1977 | Grams et al. | 600/211 X |
| 4,457,300 | 7/1984 | Budde | 600/228 |
| 4,461,284 | 7/1984 | Fackler | 128/20 |
| 4,616,634 | 10/1986 | Vargas Garcia | 600/210 |
| 4,616,635 | 10/1986 | Caspar et al. | 128/20 |
| 4,617,738 | 10/1986 | Kopacz | 30/339 |
| 4,637,377 | 1/1987 | Loop | 128/1 |
| 4,726,356 | 2/1988 | Santilli et al. | 128/20 |
| 4,949,707 | 8/1990 | LeVahn et al. | 128/20 |
| 4,973,300 | 11/1990 | Wright | 600/37 |
| 5,133,724 | 7/1992 | Wilson, Jr. et al. | 606/151 |

(List continued on next page.)

FOREIGN PATENT DOCUMENTS

| | | |
|---|---|---|
| 2216893 | 2/1999 | Canada . |
| 630 629 | 12/1994 | European Pat. Off. . |
| 668 058 | 8/1995 | European Pat. Off. . |
| 1019217 | 10/1952 | France . |
| 90 04 5130 | 6/1990 | Germany . |
| 970751 | 8/1997 | Norway . |
| 970752 | 8/1997 | Norway . |
| 970753 | 8/1997 | Norway . |
| 970754 | 8/1997 | Norway . |
| 2233561 | 1/1991 | United Kingdom ............. 600/234 |
| WO 87/04081 | 7/1987 | WIPO . |
| WO 94/14383 | 7/1994 | WIPO . |
| WO 95/17127 | 6/1995 | WIPO . |
| WO 97/10753 | 3/1997 | WIPO . |
| WO 98/27869 | 7/1998 | WIPO . |

OTHER PUBLICATIONS

Pilling Co., Pilling Surgical Instruments Catalog 1993, p. 304, "Riahi Coronary Compressor".
Scanlan International Cardiovasive Retractor System, Catalog No. 8008–109 Brochure, Pre May 1997.

(List continued on next page.)

*Primary Examiner*—Danton D. DeMille
*Assistant Examiner*—Denise Pothier
*Attorney, Agent, or Firm*—Richard D. Allison; Thomas J. DesRosier

[57] ABSTRACT

An apparatus for stabilizing a predetermined area on a heart of a patient to enable a surgical procedure, the apparatus comprising a bifurcated member having two elongated prongs which can be adjustable as to width and an elongated handle segment attached to the bifurcated member. The handle segment can be either fixably or pivotably attached to the bifurcated member. The apparatus may further comprise an attachment or inlay to prevent lateral movement thereof when being used in the surgical procedure. The apparatus may also include a cleat for securing a portion of the surgical thread used during the surgical process. At least a portion of the prongs (or feet) of the bifurcated member may further be independently rotatable for self-alignment with the surface of the predetermined area of the heart.

16 Claims, 7 Drawing Sheets

U.S. PATENT DOCUMENTS

| | | | |
|---|---|---|---|
| 5,167,223 | 12/1992 | Koros et al. | 600/232 |
| 5,201,325 | 4/1993 | McEwen et al. | 600/202 X |
| 5,222,976 | 6/1993 | Yoon | 606/223 |
| 5,318,013 | 6/1994 | Wilk | 600/225 X |
| 5,337,736 | 8/1994 | Reddy | 600/217 |
| 5,339,801 | 8/1994 | Poloyko et al. | 128/20 |
| 5,381,788 | 1/1995 | Matula et al. | 128/20 |
| 5,391,147 | 2/1995 | Imran et al. | 604/95 |
| 5,429,118 | 7/1995 | Cole et al. | 600/121 |
| 5,449,374 | 9/1995 | Dunn et al. | 600/214 X |
| 5,498,256 | 3/1996 | Furnish | 606/1 |
| 5,509,890 | 4/1996 | Kazama | 600/37 |
| 5,514,075 | 5/1996 | Moll et al. | 600/202 |
| 5,518,503 | 5/1996 | Rooney et al. | 600/240 |
| 5,529,571 | 6/1996 | Daniel | 600/213 X |
| 5,558,621 | 9/1996 | Heil | 600/201 X |
| 5,662,676 | 9/1997 | Koninckx | 600/210 X |
| 5,749,892 | 5/1998 | Vierra et al. | 600/204 |
| 5,755,661 | 5/1998 | Schwartzman | 600/204 X |
| 5,782,746 | 7/1998 | Wright | 600/37 |
| 5,875,782 | 3/1999 | Ferrari et al. | 128/898 |
| 5,888,247 | 3/1999 | Benetti | 623/66 |
| 5,894,843 | 4/1999 | Benetti et al. | 128/898 |

OTHER PUBLICATIONS

"Cardiac Retractor for Coronary Bypass Operations," John A. Rousou, MD, et al., *The Annals of Thoracic Surgery*, 1991, 52: 877–78.

"A New Retractor to Aid in Coronary Artery Surgery," A.J. DelRossi, MD, G.M. Lemole, MD, *The Annals of Thoracic Surgery*, vol. 36, No. 1, 101–02, Jul. 1983.

"New Helper Instrument in Cardiac Surgery," D. Roux, MD, et al., *The Annals of Thoracic Surgery*, 1989, 48: 595–6.

"Aortic Spoon–Jaw Clamp for Aorta–Saphenous Vein Anastomosis," Francis Robicsek, M.D., *Journal of Cardiac Surgery*, 1995; 10:583–585.

"Technique of Dissecting the Internal Mammary After Using the Moussalli Bar," R.I. Hasan, et al. *European Journal of Cardiothoracic Surgery*,4:571–572, 1990.

"Self–Retaining Epicardial Retractor for Aortocoronary Bypass Surgery," Victor Parsonnet, MD, et al., *The Journal of Thoracic and Cardiovascular Surgery*, 629–30, 1979.

"A New Internal Mammary Artery Retractor," M. Bugge, *Thoracic Cardiovascular Surgeon* 38, 316–17 (1990).

"A Simple Inexpensive Method of Heart Retraction During Coronary Artery Bypass Surgery," G.D. Angelini, MD, M.Ch., F.R.C.S., *The Annals Thoracic Surgery* 46:246–47, Aug. 1988.

A New Device for Exposing the Circumflex Coronary Artery, Akio Matsuura, MD, et al., *The Annals of Thoracic Surgery* 1995; 59:1249–50.

"Correspondence and Brief Communications," *Archives of Surgery*, vol. 115, 1136–37, Sep. 1980.

"Internal Mammary Artery Dissection: A Three Dimensional Sternal Retractor," D. Roux, MD, et al., *Journal Cardiovasic Surgery*, 30, 996–97, 1989.

"Off–Bypass Coronary Bypass Grafting Via Mimithoracotomy Using Mechanical Epicardial Stabilization," Jochen Cremer, MD, et al., *The Annals of Thoracic Surgery* 1997; 63:S79–83.

"Single Coronary Artery Bypass Grafting—A Comparison Between Minimally Invasive 'Off Pump' Techniques and Conventional Procedures," Johannes Bonatti, et al., *European Journal of Cardio–Thoracic Surgery*, 14 (Suppl. I) (1998) S7–S12.

"Less Invasive Coronary Surgery: Consensus From the Oxford Meeting," Stephen Westaby, FRCS, and Federico J. Benetti, MD, *The Annals of Thoracic Surgery* 1996; 62:924–31.

"Mini–Sternotomy for Coronary Artery Bypass Grafting," Kit V. Arom, MD, PhD, et al., *The Annals of Thoracic Surgery* 1996; 61:1271–2.

"Limited Access Myocardial Revascularization," Denton A. Cooley, MD, Texas Heart Institute Journal, vol. 23, No. 2, 1996.

"Mini–Sternotomy for Coronary Artery Bypass Grafting," *The Annals of Thoracic Surgery*, 1996; 62:1884–85.

"The Cardiac Rag—Simple Exposure of the Heart," Michael M. Bedellino, MD, et al., *Texas Heart Institute Journal*, vol. 15, No. 2, 1988, 134–35.

"Fabric Heart Retractor for Coronary Artery Bypass Operations," Shigeru Kazama, MD, et al., *The Annals of Thoracic Surgery* 1993; 55:1582–3.

"Minimally Invasive Coronary Artery Bypass Grafting," Antonio M. Calafiore, MD, et al., *The Annals of Thoracic Surgery*, 1996; 62:1545–8.

"Improved Visualization of the Internal Mammary Artery With a New Retractor System," John Pittman, MD, et al., *The Annals of Thorac Surg*, 1989; 48:869–70.

"A Modified Sternal Retractor," Nelson Ancalmo, MD, and John L. Ochsner, MD, Aug. 8, 1975.

"A Versatile Retractor for Use in Harvesting the Internal Mammary Artery and Performing Standard Cardiac Operations," Steven J. Phillips, MD, and Marge Core, RN, *The Journal of Thoracic Surgery*, 1989; 97: 633–35.

"Surgical Management of Diseased Intracavitary Coronary Arteries," John L. Ochsner, MD and Noel L. Mills, MD, *The Annals of Thoracic Surgery*, vol. 38, No. 4, 356–62 (Oct. 1984).

"Technique of Internal Mammary—Coronary Artery Anastomosis," *The Journal of Cardiovascular Surgery*, 78: 455–79, 1979.

"Graduated Probes for Coronary Bypass Surgery," George E. Green, MD, *The Journal of Thoracic and Cardiovascular Surgery*, vol. 68, No. 3, 424–27 (Sep. 1974).

"A Modified Sternal Retractor for Exposure of the Internal Mammary Artery," Peter P. McKeown, MB,BS, et al. *The Society of Thoracic Surgeons*, 1980.

"A New Concept in Sternal Retraction: Applications for Internal Mammary Artery Dissection and Valve Replacement Surgery," Aurelio Chaux, MD, and Carlos Blanche, MD, *The Annals of Thoracic Surgery*, 473–74, Oct. 1986.

The Japanese Journal of Thoracic Surgery, 1989, vol. 42, No. 2 (translation of summary included).

"Tecnica Operatoria," Minerva Cardioangiologica, vol. 23—N. 6–7 (1975) (translation of summary included).

"Microsurgery: The New Frontier," V. Mueller, 1968.

"Neurosurgical Instruments," V. Mueller, Untilted Medical Device Catalog, I17–I18, 1988.

"Heart Retractor for Use in Anastomosis in Coronary Artery By–Pass Surgery," *Japanese Journal of Thoracic Surgery*, vol. 40, No. 1, 1987 (translation of summary included).

Aesculap® General Surgical Catalogue (C–214730), Feb. 1983 (4 pages).

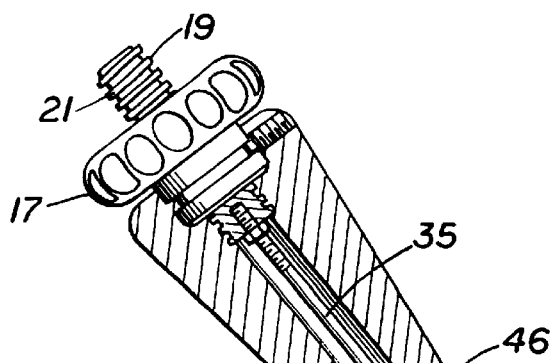
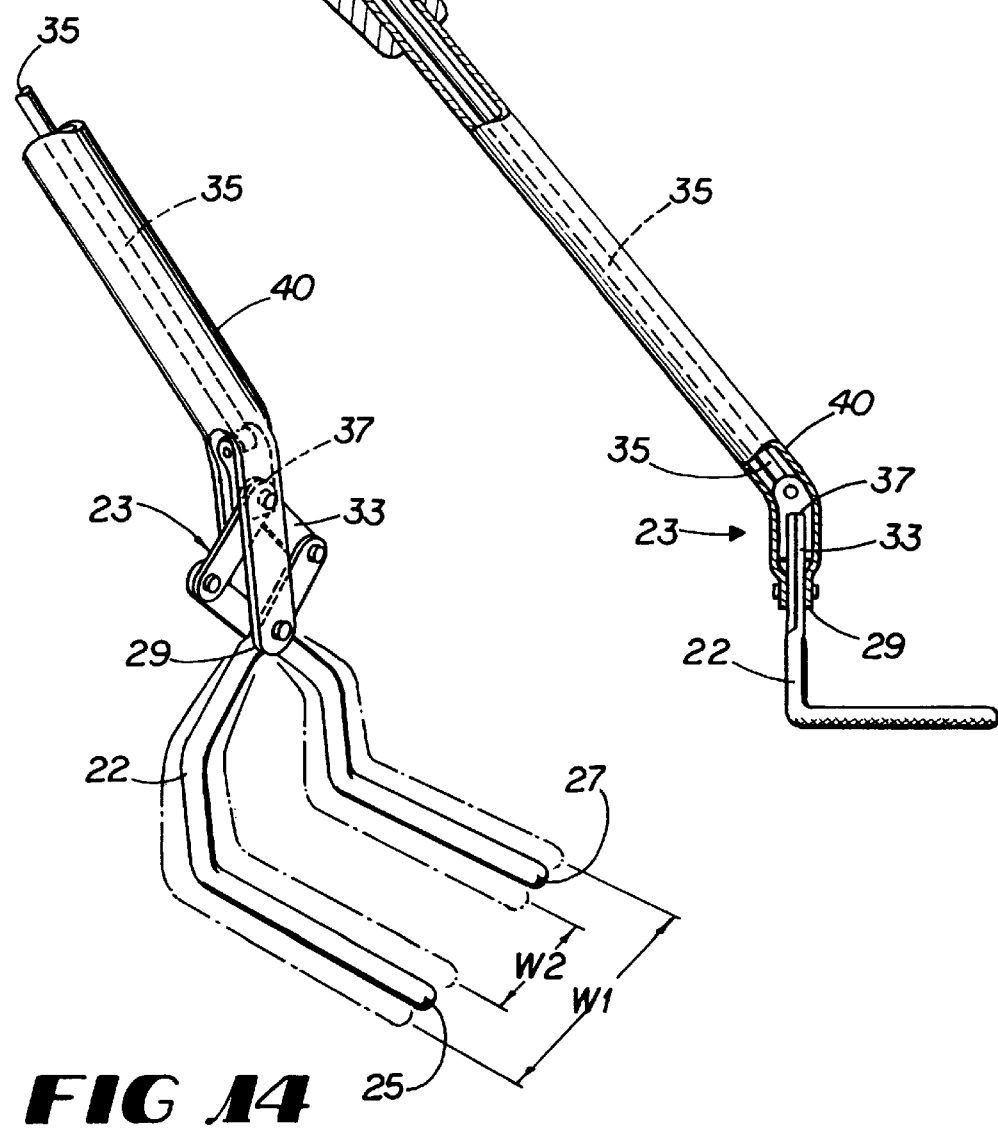
FIG. 13
FIG. 14

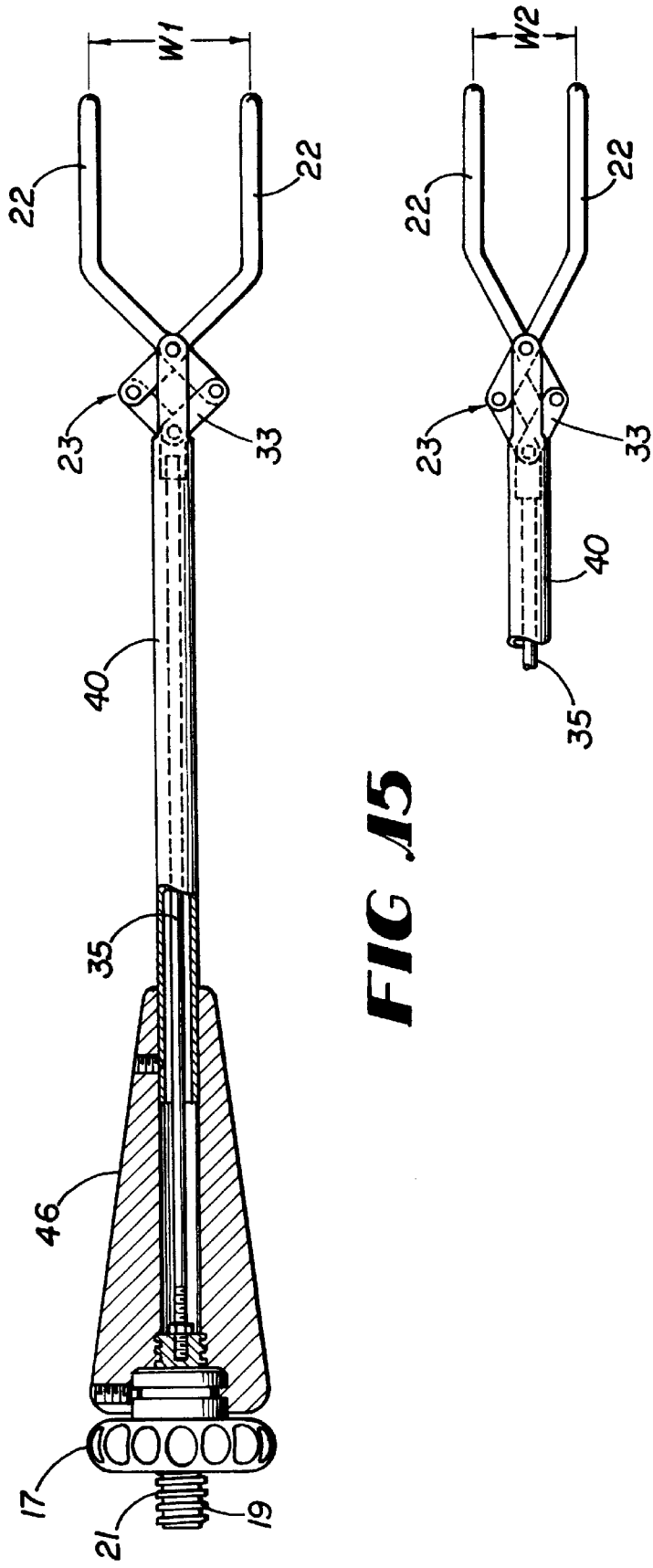

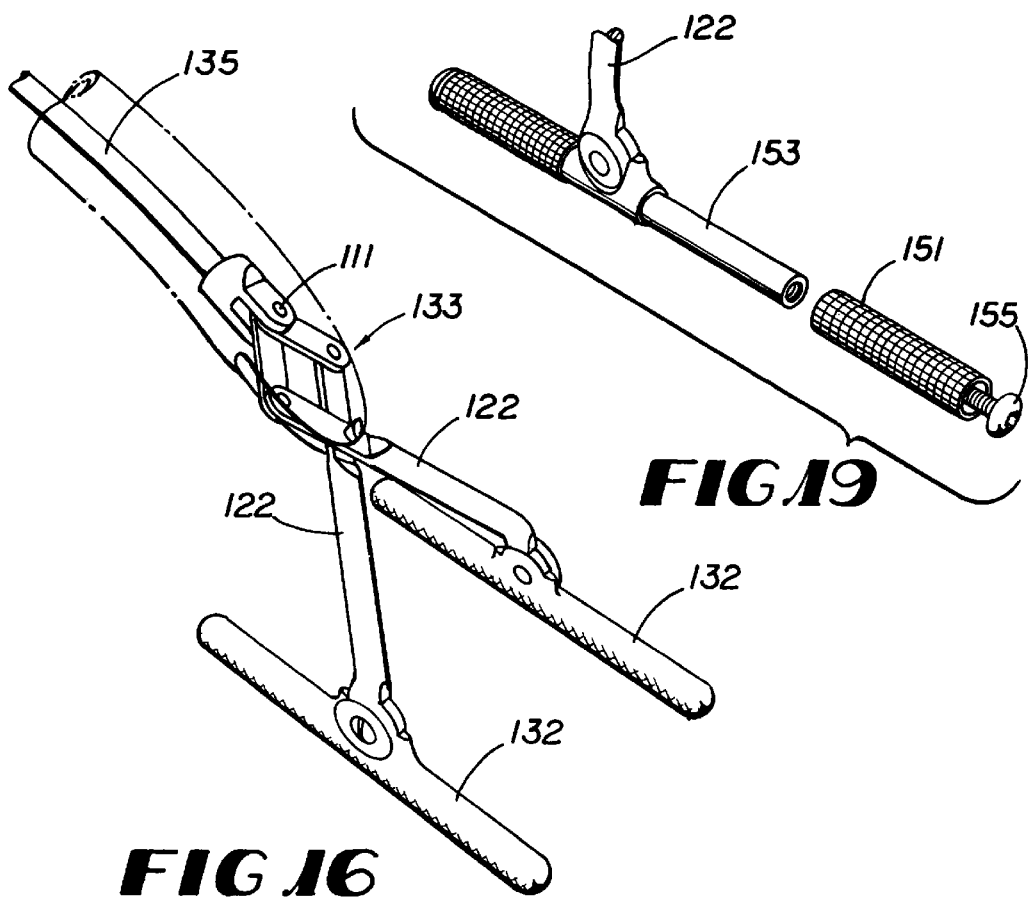
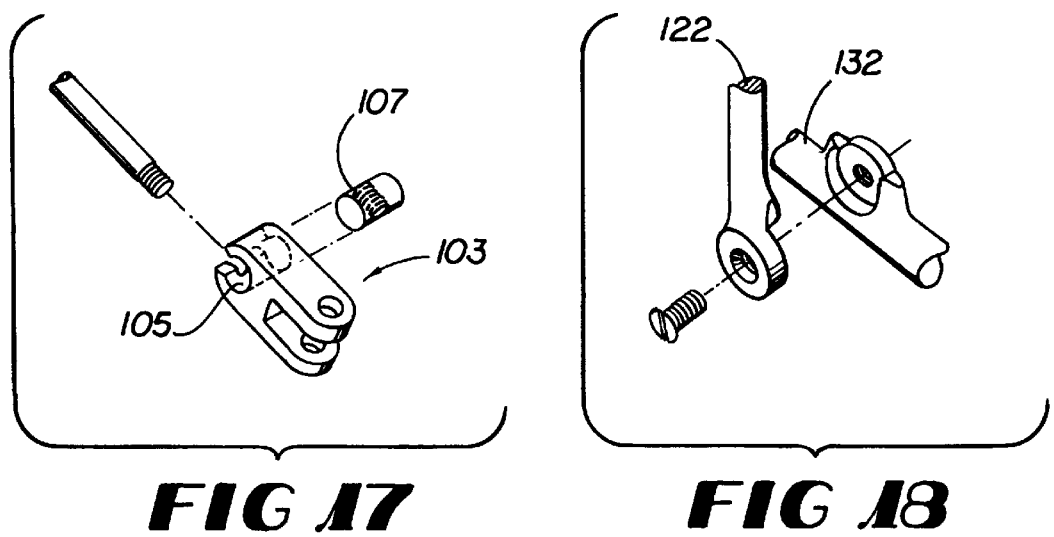

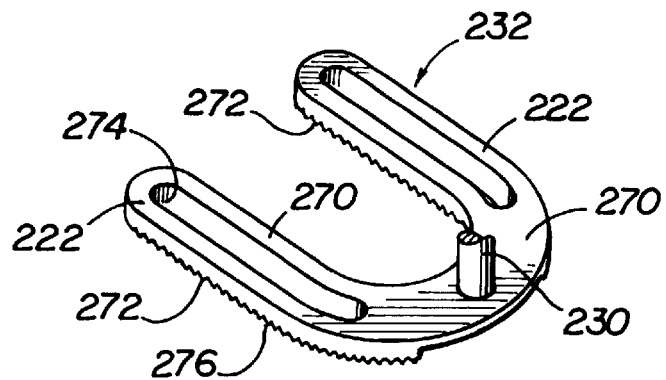
FIG 20
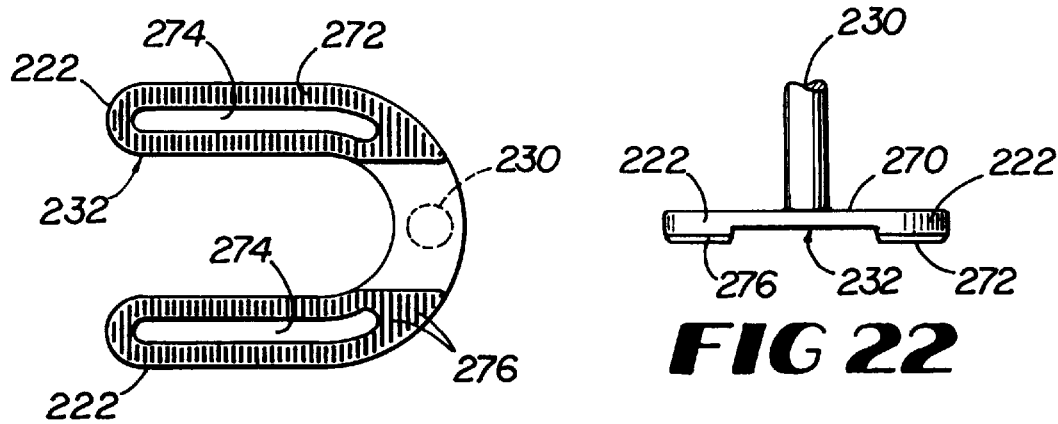
FIG 22
FIG 21
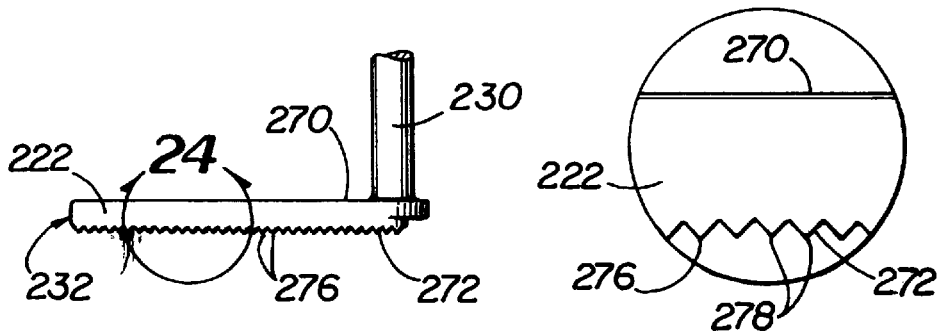
FIG 23    FIG 24

ADJUSTABLE MULTI-PURPOSE CORONARY STABILIZING RETRACTOR

This application is a continuation-in-part of Ser. No. 08/639,214, filed on Apr. 26, 1996 and also claims priority to Provisional Application Ser. No. 60/026,905, filed on Sep. 26, 1996.

BACKGROUND OF THE INVENTION

1. Field of the Invention

This invention relates to an apparatus for stabilizing a predetermined area of the body during surgical intervention, which better enables a surgeon to perform a surgical procedure at the predetermined site. In particular, the invention relates to a hand held or retractor mounted apparatus for stabilizing a predetermined area of the heart for performing minimally invasive coronary artery bypass grafting at the surgical site which has adjustable tool end comprised of substantially at least two parallel prongs (tines or feet) with actuator means to allow for adjustment of the spacing between the tines and wherein the tines are also moveable so as to be self-aligning with the surface of the heart.

2. Background Art

Atherosclerosis or coronary artery disease is among the most common and serious health problems confronting the medical profession. In the past, many different approaches at therapy have been utilized. Surgical correction of occluded or stenosed coronary arteries via bypass grafting through conventional approaches, such as the sternotomy, are probably still the most common procedure performed today, especially where multiple bypass grafts are needed.

However, interventional techniques, such as percutaneous transluminal angioplasty (PTCA), have gained popularity as the method of choice for therapy of atherosclerotic occlusions for several reasons. The transluminal approach is a minimally invasive technique which subjects the patient to less trauma and less recovery time, especially when compared to bypass grafts which utilize homologous tissue, such as saphenous vein grafts. Often the patient suffers complications at the graft donor site which are worse than the sternotomy and anastomosis.

Although PTCA procedures are often successful, complications such as restenosis or thrombosis and embolism can occur. Intravascular stents are sometimes deployed at the PTCA site to lessen the occurrence of restenosis. However, restenosed vessels often require surgical intervention for correction.

Surgical correction of restenosis, as well as conventional bypass graft surgery, require that the heart be stopped and the patient placed on a heart/lung bypass machine during the procedure. This occurs at considerable expense and risk to the patient. In an effort to reduce the expense, risk and trauma to the patient, physicians have recently turned to minimally invasive surgical approaches to the heart, such as intercostal and endoscopic access to the surgical site. In addition, utilization of alternative graft vessels, such as the internal mammary artery (IMA), have also greatly reduced the trauma to the patient and increased the efficacy of surgical therapy.

Prior to the present invention, however, attempts at performing minimally invasive bypass grafting on a beating heart were thought to be too tedious, dangerous and difficult because of the delicate nature of the surgical procedure, the lack of adequate access through a reduced surgical field, and the lack of a way to adequately stabilize and reduce movement at the graft site. Such a minimally invasive bypass grafting performed on the beating heart eliminates the expense and risk of stopping the heart and the necessity of the heart lung bypass machine and decreases patient recovery time. For single or double bypass procedures, especially where the IMA is utilized, patient trauma and recovery time is even further decreased.

SUMMARY OF THE INVENTION

The above problems of the prior art are overcome by the present invention which provides an apparatus for stabilizing a predetermined area on a heart or other organ of a patient to enable a surgical procedure to be performed. The apparatus of the present invention comprises a bifurcated member having at least two elongated prongs, an elongated handle segment, and a means for joining the handle member to the bifurcated member. Each prong of the bifurcated member may have a first section, a second section, and a third section. The first section is adjacent the handle segment and terminates in the second section. The second section engages the heart or other organ that the surgical procedure occurs and terminates in the third section.

In one embodiment the bifurcated prongs (tines or feet) may be substantially parallel to one another along at least a portion of their bodies and may further comprise a means for movement of the tines between an open and a closed position to increase or decrease the width or spacing between the parallel portions. The moving means can comprise a scissor hinge assembly attached to an actuator rod which passes through a bore in the handle to means for selective movement of the actuator rod allowing the surgeon to space the tines at a desired distance (width) apart.

Since the second section engages the heart, it is desired that the second section further comprises a means for stabilizing it from sliding on the heart. Stabilizing the apparatus on the heart is an important consideration during the surgical procedure. The present invention can encompass many different stabilizing means, including, for example, a textured portion on at least a portion of one second section, an insert disposed on the second section having a plurality of teeth, an insert having a plurality of flexible hooks, an insert having a plurality of bristles, or even a flexible covering disposed over at least a portion of the second section. The flexible covering can be a cloth, such as cotton, or a tubular member formed from a material such as silicon.

In a further embodiment, the section which engages the heart can be fenestrated using slots or holes interspersed between or among a textured gripping surface. When this section is applied to the surface of the heart, a portion of the heart tissue gently and atraumatically pouches up into or fills the fenestrations or openings to further stabilize the heart and prevent slippage of the stabilizing device at the desired surgical site.

One embodiment of the invention comprises bifurcated prongs wherein a first portion terminates in a means for allowing rotational movement of a second and or third portion in a desired plane that can be generally perpendicular to the longitudinal axis of the first portion. Rotational stops can be placed on the first and second portions to limit the rotational movement to a desired range. The independently rotatable portion, e.g., a prong, tine or foot is self-aligning with the surface of the heart in the deployed position.

Another aspect of the present invention is that it further comprises a means for securing a portion of a surgical thread that can be used in the surgical procedure. In the preferred embodiment, the securing means comprises at least one cleat disposed on the apparatus. The cleat or cleats can be disposed in the end of the third section of each of the prongs and/or disposed on the handle segment or the bifurcated member adjacent the first section or both.

In another embodiment of the present invention, the joining means comprises a means for pivotally connecting the handle segment to the bifurcated member. This can be achieved by a socket disposed on the handle segment and a ball joined to the bifurcated member, wherein the ball is sized to be complementarily received within the socket. To facilitate use of the present invention, it preferably further comprises a means for locking the ball in a selective position within the socket so that the handle segment is disposed at a desired pivotal orientation relative to the bifurcated member.

Thus, it is an object of the invention to provide an apparatus for stabilizing a predetermined area of the heart of a patient to enable a surgeon to perform a surgical procedure at the predetermined site.

It is another object of the invention to provide an apparatus which stabilizes a predetermined area of a beating heart to enable a surgeon to perform a surgical procedure at the predetermined site.

A further object of the invention is to provide an apparatus for stabilizing a predetermined area of the heart which further comprises means for anchoring tension or ligation sutures.

Yet another object of the invention is to provide an apparatus for stabilization of an area of the beating heart adjacent to a coronary artery for performing coronary artery bypass grafting.

Another object of the invention is to provide an apparatus as above which is further adapted for pivotal attachment to a device which provides access to the surgical site such as a rib spreader or other retractor.

Another object of the invention is to provide an apparatus for stabilization of a predetermined area of the body to enable a surgical procedure at the predetermined site.

A further object of the invention is to provide an apparatus which is capable of stabilizing a predetermined area of the body that can also function as a tissue retractor to assist the surgeon in accessing the surgical site.

It is another object of the invention to provide an apparatus which has adjustable substantially parallel prongs (tines or feet) which allow the surgeon to preselect the width or distance between the prongs.

It is yet another object of the invention to provide an apparatus having prongs (tines or feet) which are independently rotatable and self aligning with the surface of the heart when in the deployed position.

It is another object of the invention to provide an apparatus which has fenestrated using slots or holes interspersed between or among a textured gripping surface on the prongs (tines or feet) such that when applied to the surface of the heart, a portion of the heart tissue gently and atraumatically pouches up into or fills the fenestrations or openings to further stabilize the heart and prevent slippage at the predetermined surgical site.

The above recited objects of the invention are not intended to so limit the used of the invention. These and other objects of the invention will be apparent to the skilled artisan based upon the following disclosure.

BRIEF DESCRIPTION OF THE DRAWINGS

FIG. 13 is a cut away perspective view of one embodiment of the invention showing means for actuation of the bifurcated prongs (tines or feet), including a scissors linkage assembly, actuator rod and prong (or tine) width adjustment knob and boss assembly on the handle.

FIG. 14 is a perspective view of the adjustable width prongs (or tines).

FIG. 15 is a perspective (or top plan) view of the embodiment of the invention shown in FIG. 14 with the prongs (or tines) in the open position.

FIG. 15A shows the prongs (or tines) in the closed position.

FIG. 16 is a perspective view of one embodiment of the invention showing independently rotatable prongs (tines or feet) and means for actuation of the scissor extension links (or a first section of the prongs).

FIG. 17 shows an alternate means for linkage of the actuator rod to the scissors linkage assembly shown in FIG. 16.

FIG. 18 is an exploded view of the rotational mechanism and stops of the rotating prongs (tines or feet) shown in FIG. 16.

FIG. 19 shows an alternate embodiment of the invention wherein rotatable textured sleeves are covering a portion of the prongs (tines or feet) shown in FIG. 16.

FIG. 20 is a perspective view of an alternate embodiment of the stabilizing tines or prongs showing fenistrations or holes through the tines for capturing cardiac tissue to increase stabilization at the predetermined site.

FIG. 21 is a bottom plan view of the embodiment shown in FIG. 20.

FIG. 22. is an rear elevational view of the embodiment shown in FIG. 20.

FIG. 23 is side elevational view of the embodiment shown in FIG. 20.

FIG. 24 is an enlargement of the inset at circle 24 of FIG. 23 showing the textured surface of the bottom of the tines or prongs.

DETAILED DESCRIPTION OF THE INVENTION

The present invention is more particularly described in the following examples which are intended as illustrative only since numerous modifications and variations therein will be apparent to those skilled in the art. As used in the specification and in the claims, "a" can mean one or more, depending upon the context in which it is used.

The present invention, as shown in FIGS. 1–12, encompasses an apparatus 10 for stabilizing a predetermined area on a heart 2 of a patient to enable a surgical procedure to be performed. The apparatus 10 comprises a bifurcated member 20, an elongated handle segment 40, and a means for joining the handle segment 40 to the bifurcated member 20. It is preferred that the bifurcated member 20 and the handle segment 40 be constructed of stainless steel or other acceptable material for surgical instruments.

It can be appreciated by one skilled in the art that the apparatus of the present invention can be utilized at any location on or within the body where tissue stabilization or isolation of a predetermined area is desired, including but not limited to the heart, liver kidneys, bladder, stomach, intestines, and vascular and other soft tissue surgery. As set forth in greater detail below, the unique design of the apparatus also provides the added feature of using the apparatus as a tissue retractor for use, e.g., in gaining access to a predetermined surgical site.

Figure 1:
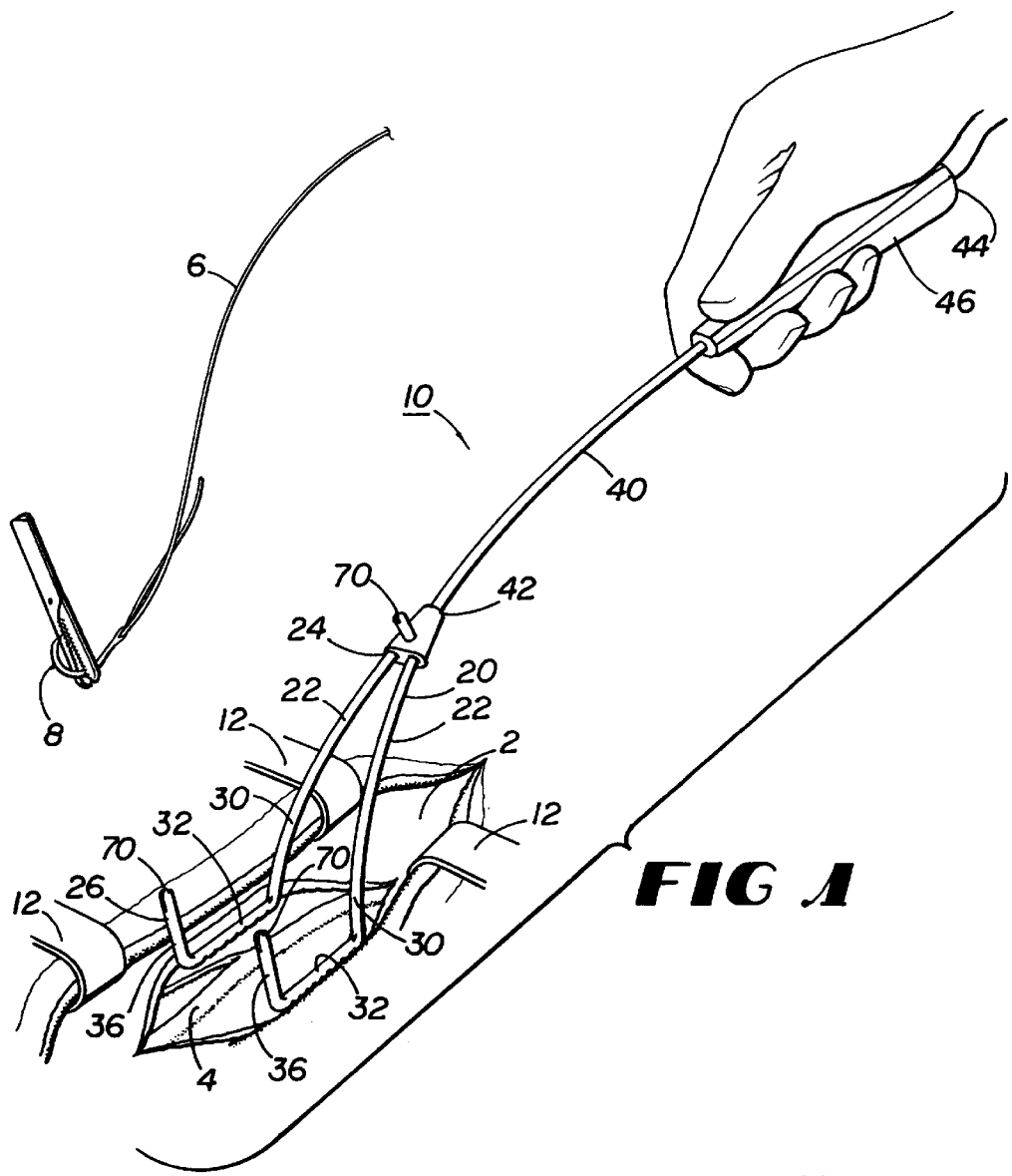
FIG. 1 is a perspective view of one embodiment of the present invention showing the apparatus being place on the heart of a patient to perform a surgical procedure.

The present invention is ideal for use in heart surgery, in either conventional open heart surgery or by minimally invasive surgery, e.g., minimally invasive coronary artery bypass grafting. For minimally invasive surgery, access to the heart 2 may be achieved through the ribs of the patient using a rib spreader 12, as shown in FIG. 1. In the typical procedure, the surgeons will usually access the heart via the fourth intercostal space located between the third and fourth ribs, but this may be changed based on the individual patient's anatomy. Since, for the above reasons, this procedure is sometimes performed on a beating heart 2, it is advantageous to stabilize the heart 2 in the area that the surgical procedure will occur. Thus, the apparatus of the present invention can be used in a manner (as shown in FIG. 1) such that the second section 32 engages the surface of the heart 2. A slight compressive force is placed on the heart 2 by the apparatus 10 in the area that the surgical procedure will occur so that the heart's movement at that specific area is diminished and stabilized. The stabilizing of the heart 2 is particularly useful for a heart suturing technique in the area of the coronary arteries such as the anastomosis of a bypass graft. In particular, it is advantageous to place a traction suture around an artery 4 using a needle 8 and suture thread 6 while the present invention is stabilizing the surface of the heart 2 adjacent to the artery 4.

The elongated handle segment 40 is used to extend the bifurcated member 20 into the chest of the patient to reach the surface of the heart 2. The handle segment 40 has a first end 42 and an opposite second end 44. As shown in FIG. 1, the handle segment 40 preferably has a hand grip 46 disposed on its second end 44.

Figure 2:
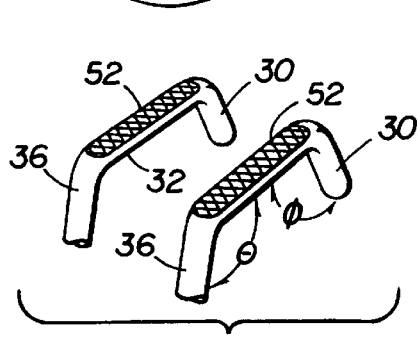
FIG. 2 is a perspective view of one embodiment the stabilizing means of the present invention comprising a textured portion on the second surface of the prongs of the bifurcated member.
Figure 3:
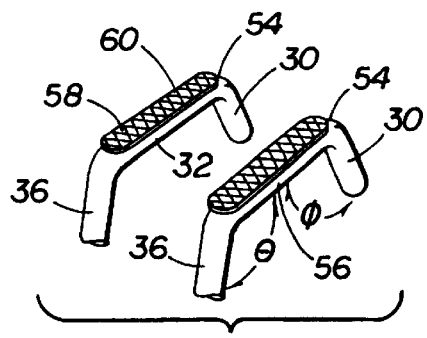
FIG. 3 is an alternative embodiment of FIG. 2 in which the stabilizing means comprises an insert having a plurality of teeth.
Figure 4:
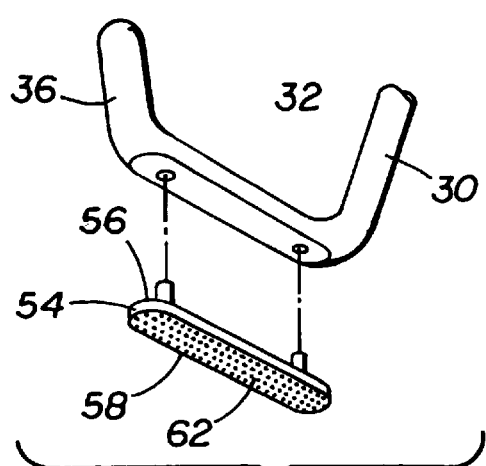
FIG. 4 is an alternative embodiment of FIG. 2 in which the stabilizing means comprises a plurality of flexible hooks.

Still referring to FIG. 1, the bifurcated member 20 comprising two elongated prongs 22. Each prong 22 has a proximal end 24 and an opposite distal end 26. Each prong is divided into three sections, a first section 30, a second section 32, and a third section 36. The first section 30 is adjacent the proximal end 24 and terminates in the second section 32. The second section 32 engages the heart 2 and terminates in the third section 36, which is adjacent the distal end 26. It is also preferred that the second sections 32 of each of the two prongs 22 are in the same plane, which is shown in FIGS. 1–3.

As can be appreciated, the apparatus 10 of the present invention can be used in surgical procedures other than heart surgery, including, for example, soft tissue procedures such as vascular thrombosis repair, intestinal resection and anastomosis and other intra abdominal procedures, and the like.

Although including the third section 36 is preferred, a contemplated alternate embodiment does not include this third section 36. However, this embodiment is less desirable. One primary reason is the third section 36 can be used as a tissue retractor or a retractor to pull a selected item, such as surgical thread 6, away from the area that the surgical procedure is being performed. In addition, the third section 36 can be advantageously positioned to secure surgical thread 6 in a cleat 70, which is discussed below.

For use in heart surgery, the apparatus 10 has certain size limitations. For example, the available area to a surgeon to perform a minimally invasive surgical procedure on the heart 2 via an intercostal approach is approximately three (3) inches by one and a half (1½) inches. Accordingly, it is desired that the width between the second sections 32 be in the range of one half (½) to one and a quarter (1¼) inches, more preferably in the range of three quarters (¾) of an inch to one (1) inch. These widths are narrow enough to fit into the confined space, yet wide enough to bridge the area of interest, e.g., bridge the artery 4 that is to be bypassed, as shown in FIG. 1.

In a preferred embodiment, the range for the length of the second section 32 is in the range of one half (½) inch to one (1) inch, more preferably in the range of two-thirds (⅔) Of an inch to three quarters (¾) of an inch. In the preferred embodiment, each second section 32 is three quarters (¾) of an inch long and separated by three quarters (¾) of an inch from the other second section 32.

The juncture between the first section 30 and the second section 32 forms at least a 90°, or right, angle φ therebetween. It is preferred that the angle φ be obtuse so that the surgeon has uninhibited access to the area that the surgical procedure is occurring. An acute angle could be used in the present invention, but it is less desirable because it would likely interfere with the surgical procedure.

Similarly, it is preferred that the juncture between the second section 32 and the third section 36 also form either a right or an obtuse angle θ therebetween. Although an acute angle is likewise an option, the same problem arises with the interference with the surgical procedure as with angle φ. Also, for certain embodiments, it may be desired to use different angles θ in the two prongs. In the preferred embodiment, however, each prong 22 is substantially "U" shape in side view, which can be appreciated from FIG. 1 and also from FIGS. 2 and 3, which show a truncated inverted "U" shape.

Since the second section 32 engages the heart 2, it is preferable that this section 32 further comprise a means for stabilizing the second section 32 from sliding on the heart 2. The stabilizing means, in other words, resists sliding or slipping motion between the surface of the heart 2 and the second section 32. Obviously, the stabilizing means should not be of a type that may potentially damage tissue of the heart 2 or other vital organs with which the apparatus 10 is used.

In one embodiment shown in FIG. 2, the stabilizing means comprises a textured portion 52 on the second section 32. The surface shown in FIG. 2 is a knurled texture. Other embodiments are contemplated, such as a plurality of intersecting slits therein that prevent the second section 32 from sliding when it engages the heart 2. As can be appreciated, any configuration for the surface of the stabilizing means can be utilized so long as the stabilizing means atraumatically grips the tissue.

Referring to FIG. 3, the stabilizing means can comprise an insert 54 having an attaching surface 56 secured to the second section 32 of each prong 22 and an opposite stabilizing surface 58 which carries the stabilizing means. In FIG. 3, the stabilizing surface 58 of the insert 54 comprises a plurality of tungsten carbide teeth 60. Other materials may be used, however, including stainless steel. As one skilled in the art will appreciate, the teeth should be aggressive enough to prevent sliding, but not so aggressive that they could potentially damage the surface of the heart 2. Now referring to FIG. 4, stabilizing surface 58 of the insert 54 comprises a plurality of flexible hooks 62. The preferred hooks are those of a hook and loop fastener, commonly referred to as VELCRO® fasteners.

Figure 5:
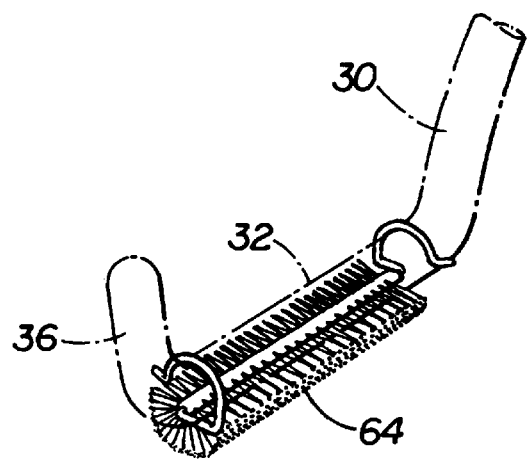
FIG. 5 is an alternative embodiment of FIG. 2 in which the stabilizing means comprises a plurality of bristles.

Still another embodiment of the stabilizing means is shown in FIG. 5, in which the stabilizing means comprises a plurality of bristles 64. The bristles 64 are disposed at a plurality of different orientations, similar to that of a tube or glass cleaner. Because of the multiple orientations of the bristles 64, any direction that the second section 32 tends to slide is resisted by bristles 64 oriented that direction, which contact the surface of the heart 2 to resist the motion.

Figure 6:
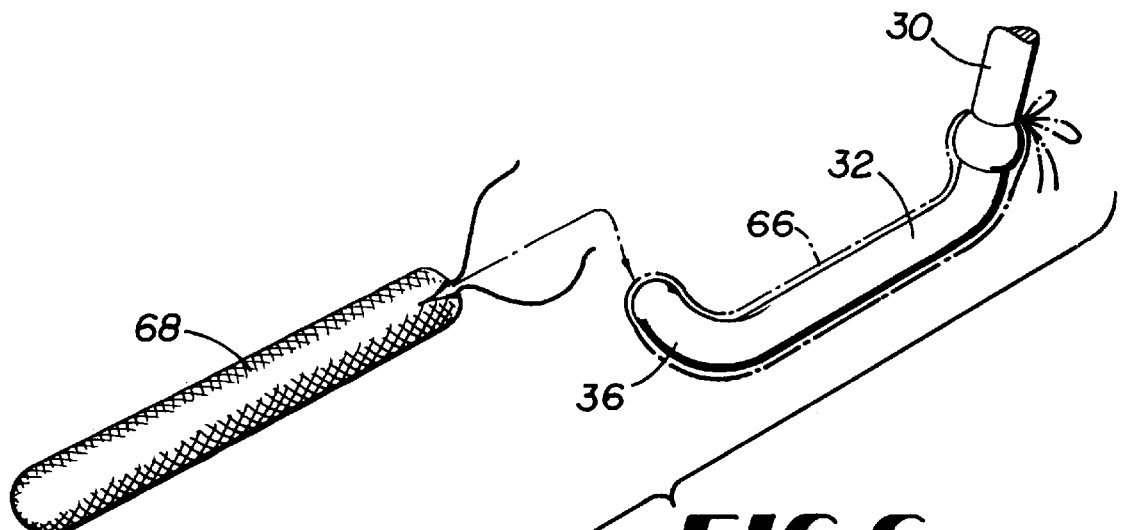
FIG. 6 is an alternative embodiment of FIG. 2 in which the stabilizing means comprises a flexible covering disposed over the second surface of the prongs of the bifurcated member.
Figure 7:
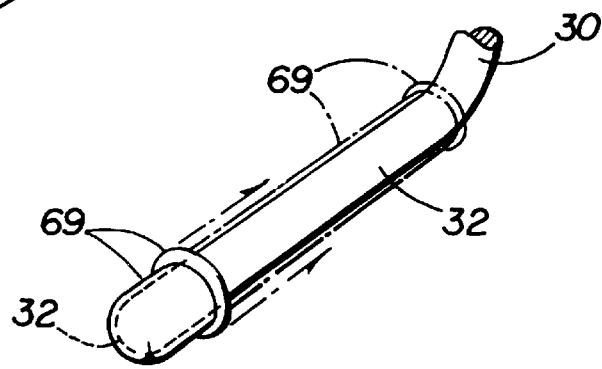
FIG. 7 is an alternative embodiment of FIG. 6 in which the flexible covering is a tubular member.

In another embodiment shown in FIG. 6, the stabilizing means comprises a flexible covering 66 disposed over at least a portion of the second section 32. The covering 66 can a cloth 68, such as cotton, braided cotton, or linen. Other coverings that resist motion when disposed on the surface of a heart 2 can also be used. In another embodiment shown in FIG. 7, the covering 66 is a tubular member 69 selected from the group of silicon, rubber, or plastic. Likewise, other materials that resist motion when disposed on the surface of a heart 2 can also be used.

Figure 8:
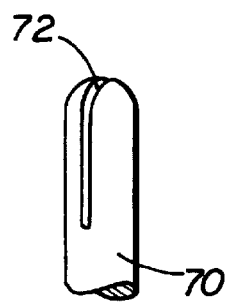
FIG. 8 is an elevated front view of one embodiment of a cleat for use with the present invention.
Figure 9:
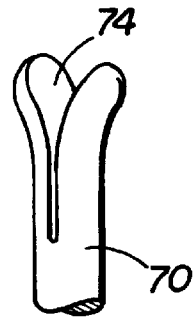
FIG. 9 is an alternative embodiment of the cleat shown in FIG. 8.
Figure 10:
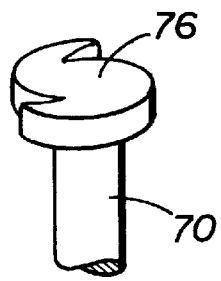
FIG. 10 is an alternative embodiment of the cleat shown in FIG. 8.
Figure 11:
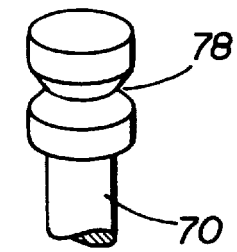
FIG. 11 is an alternative embodiment of the cleat shown in FIG. 8.

Another aspect of the present invention is that the apparatus 10 further comprises a means for securing a portion of a surgical thread 6 used in the surgical procedure. In the preferred embodiment, the securing means comprises at least one cleat 70. Referring back to FIG. 1, the cleat 70 is disposed in the distal end 26 of each of the prongs 22 of the bifurcated member 20. Some of the different embodiments for the cleat 70 are shown in FIGS. 8–11. The preferred embodiment of the cleat 70 that is disposed in the distal end 26 is a slot 72, which is shown in FIG. 8, or a slot with a curved opening 74, which is shown in FIG. 9. Other embodiments to dispose at the distal end 26 include a wedge 76, shown in FIG. 10, or a lateral "V" barrel 78, which is similar in design to a bollard and shown in FIG. 11.

Referring again to FIG. 1, it is also preferred to dispose a cleat 70 on either the first end 42 of the handle segment 40 or the proximal end 24 of the bifurcated member 20. More than one cleat 70 can be disposed in this area if the use of the present invention requires multiple cleats 70. As discussed above and shown in FIGS. 8–11, the cleat 70 can be selected from the group of a wedge 76, a lateral "V" barrel 78, a protrusion having a slot 72 therein, or a protrusion having a slot with a curved opening 74 therein. As will be appreciated by one skilled in the art, other embodiments of the present invention can use other types of cleats 70 and other locations to dispose the cleats 70.

As shown in FIG. 1, the joining means, which joins the handle segment 40 to the proximal ends 24 of the two prongs 22, comprises fixedly attaching the first end 42 of the handle segment 40 directly to the proximal end 24 of each of the two prongs 22. Alternatively, the joining means can comprise a connecting bar (not shown) disposed so that it is fixed attached to the first end 42 of the handle segment 40 to form a "T" shape. Each end of the connecting bar is fixedly attached to the proximal end 24 of a respective prong 22.

In another embodiment, the joining means further comprises a means for pivotally connecting the first end 42 of the handle segment 40 to the proximal end 24 of the bifurcated member 20. The advantage of the pivoting means is the second sections 32 can be disposed at the predetermined location with the handle segment 40 at a position that facilitates moving the bifurcated member 20. Once properly positioned, then the handle segment 40 can be pivoted to another position and, optionally, locked at that position so that the handle segment 40 does not interfere with the surgical procedure.

Figure 12:
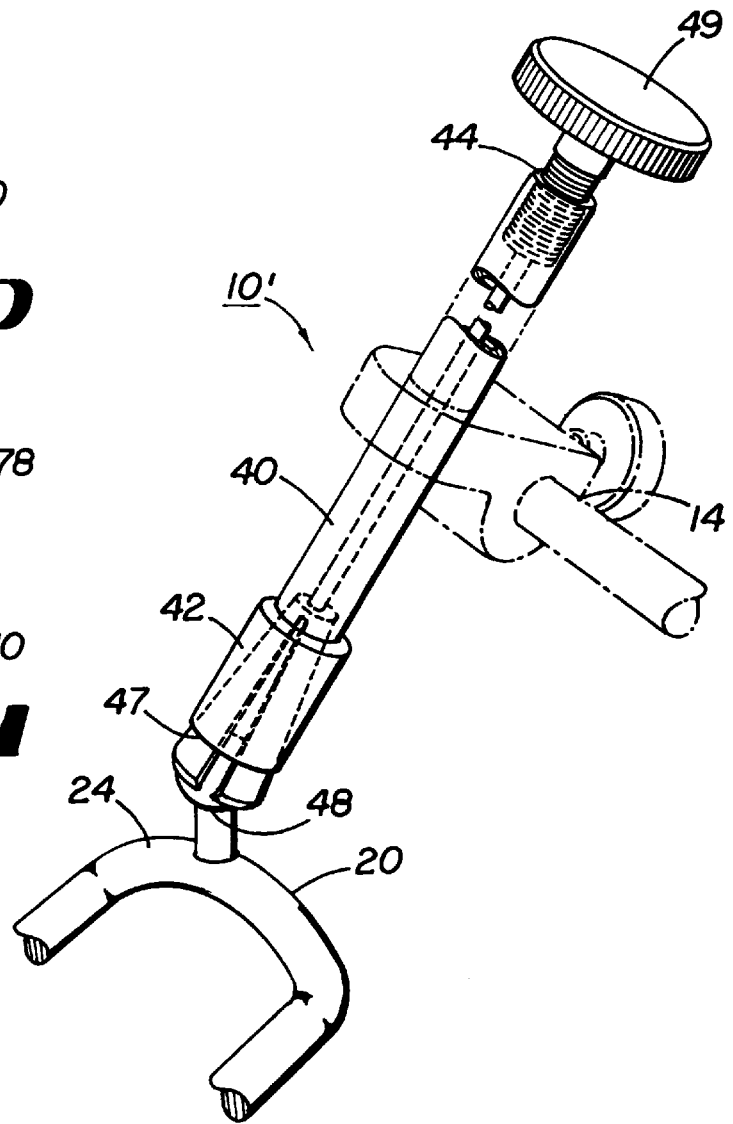
FIG. 12 is another embodiment of the present invention in which the handle is pivotally connected to the bifurcated member.

In the embodiment shown in FIG. 12, the pivotally connecting means comprises a socket 47 disposed on the first end 42 of the handle segment 40 and a ball 48 joined to the proximal ends 24 of the two prongs 22 of the bifurcated member 20. The ball 48 is sized to be complementarily received within the socket 47. Preferably, the joining means further comprises a means for locking the ball 48 in a selective position within the socket 47 so that the handle segment 40 is disposed at a desired pivotal orientation relative to the second sections 32. An example is a tightener 49 that constricts the size of the socket 47 to lock the ball 48 in the desired position. Other pivoting means are contemplated including, for example, a hinged connection (not shown) in which the handle segment 40 only pivots in a plane that is perpendicular to the plane formed by the second segments 36.

Another embodiment that is contemplated of the present invention further comprises a means for attaching the handle segment 40 to a rib spreader (not shown). Since access to the heart 2 may be achieved using a rib spreader 12, it is desired to have a means to hold the apparatus 10 at the desired stationary position. An attachment 14 to the rib spreader can serve this purpose. As one skilled in the art will appreciate, there are numerous other options available to attach the handle segment 40 mechanically so that the second section is maintained at a desired position without a person physically holding the apparatus 10.

The embodiment shown in FIGS. 13 and 14 comprises a coronary stabilizing retractor 10 of the type generally shown in FIG. 1 above but further having prongs 22 (also referred to herein as tines or feet) which have means 23 for allowing adjustment of the distance, spacing or width W1 and W2 between the distal ends 25, 27 of prongs 22. The means 23 for allowing adjustable movement of prongs 22 can be a scissors assembly as shown in FIGS. 13 and 14, however other configurations will be apparent to one of skill in the art. In the embodiment shown, handle segment 40 is hollow with an actuator rod 35 slidably disposed within the hollow lumen of handle segment 40. Actuator rod 35 is pivotally connected to scissors hinge (or linkage) assembly 33 at pivot point 37 at the proximal (or free) end of scissors hinge (or linkage) assembly 33. Scissors hinge assembly 33 is pivotally attached to hollow handle segment 40 at its distal (or stationary) end 29. The handle segment 40 is oriented at an obtuse angle relative to at least a portion of the bifurcated member.

An adjustment knob 17 is threaded complimentary to threads 19 on the adaptor 21 on proximal end of actuator rod 35 such that turning the knob clockwise as shown in FIG. 15A retracts actuator rod 35 proximally and causes movement of prongs 22 to the closed position W2. The surgeon can thus adjust the width of prongs 22 to a desired width over a range of positions between W1 and W2.

The embodiment shown in FIG. 16 shows a pair of prongs (tines or feet) 132 which are self-aligning with a surface on which they are placed (such as the heart) having rotation about an axis that is substantially perpendicular to the long axis of scissor extension links (or leg portions) 122. The pair of tines (or feet) 132 can be independently rotatable with respect to each other. The pivotal arrangement shown in FIG. 18 is a preferred means for rotational attachment of prongs (or feet) 132 to scissor extension links (or leg portions)122.

FIGS. 17 shows a preferred means for attachment of actuator rod 135 to scissors hinge (or linkage) assembly 133. Generally the attachment can be a yoke 103 having a slot 105 and complimentary barrel link 107 for threaded attachment to actuator rod 135. Alternatively, yoke 103 can be a single piece attached by a pin 111 to the scissors hinge (or linkage) assembly 133 and having a means such as a threaded engagement (not shown) for attachment to actuator rod 135.

FIG. 19 shows a further embodiment of the invention wherein the prongs (or feet) 132 are configured so as to allow positioning of a rotatable textured sleeve 151 over shank portion 153. The textured rotatable sleeves are held in place by cap screws 155.

In a further embodiment, shown in FIGS. 20–24, the second section 232 which engages the heart can be fenestrated using slots 274 or holes interspersed between or among a textured gripping surface 276. Prongs 222 of second section 232 have a top surface 270 and a bottom surface 272. Holes or fenestrations 274 extend through the body portion of prongs 222 such that hole 274 communicates the top surface 270 with the bottom surface 272. Alternatively, the fenistrations or slots in the bottom surface 272 do not have to extend all the way through the body of prongs 222 such that a cavity is created in the bottom surface.

It is desirable that the textured surface 276 be adjacent to and surround the fenistrations or holes 274 on the bottom surface 272 of prongs 222. In the embodiment shown in FIGS. 23–24, the textured surface 276 is comprised of atraumatic (non-traumatic) teeth 278 for increasing the frictional grip of prongs 222 on the surface of the heart.

When the bottom surface 272 of second section 232 is positioned on the surface of the heart at a predetermined surgical site and gentle pressure is applied, a portion of the heart tissue gently and atraumatically pouches up into or fills the fenestrations or holes 274 to further stabilize the heart and prevent slippage of the stabilizing device at the predetermined surgical site. The apparatus shown in FIGS. 20–24 can be attached via first section 230 to a handle section utilizing, e.g., a ball and socket connection as shown in FIG. 12 and described above.

Although the present process has been described with reference to specific details of certain embodiments thereof, it is not intended that such details should be regarded as limitations upon the scope of the invention except as and to the extent that they are included in the accompanying claims.

What is claimed is:

1. An apparatus for stabilizing a predetermined area of the heart of a patient to enable a surgical procedure, comprising:

a. bifurcated member comprising elongated and generally parallel prongs, each prong having a proximal end portion and an opposite distal end portion and having a first section and a second section, the first section being adjacent the proximal end portion and terminating in the second section, the second section is adapted to engage the heart and is sized to stabilize the predetermined area of the heart;

b. an elongated handle segment having a longitudinal axis and first end portion and an opposite second end portion, the elongated handle segment oriented at an obtuse angle relative to a portion of the bifurcated member;

c. a connector on the first end portion of the handle segment for joining the handle segment to the proximal end portions of the prongs of the bifurcated member;

d. a first member on the second end portion of the handle segment wherein the first member is rotatable generally about the longitudinal axis of the handle segment and movement of the prongs relative to the handle segment occurs during rotation of the first member; and e. wherein the second section of each of the prongs are oriented generally parallel to each other and the width between each of the prongs is adjustable so that the second section of each prong is movable relative to each other between first and second parallel positions.

2. The apparatus of claim 1, wherein the prongs are independently movable with respect to each other in a first position of the first member.

3. The apparatus of claim 1, wherein the prongs are independently movable with respect to the connector in a first position of the first member.

4. The apparatus of claim 1, wherein the second end portion of the handle segment includes a scissors hinge thereon for the remote movement of the prongs.

5. The apparatus of claim 1, wherein the prongs are independently alignable with respect to the predetermined area of the heart.

6. The apparatus of claim 1, wherein the connector attaches the handle segment to the prongs at a location between the distal end portion and the proximal end portion of each of the prongs.

7. The apparatus of claim 1, wherein the prongs include removable sleeves thereon.

8. The apparatus of claim 1, wherein the handle segment includes a longitudinal axis and the prongs are pivotal generally parallel to the longitudinal axis thereof.

9. An apparatus for stabilizing a predetermined area of the heart of a patient to enable a surgical procedure, comprising:

a. a bifurcated member formed by a plurality of elongated prongs, each prong having a first section and a second section;

b. an elongated handle segment having a longitudinal axis and a first end portion and an opposite second end portion, the elongated handle segment oriented at an obtuse angle relative to a portion of the bifurcated member;

c. a connector for joining the first end portion of the handle segment to the bifurcated member; and d. a first member on the second end portion of the handle segment wherein the first member is rotatable generally about the longitudinal axis of the handle segment and movement of the connector on the first end portion of the handle segment occurs in response to the rotation of the first member and wherein the second section of each of the prongs are movable relative to each other between first and second parallel positions.

10. The apparatus of claim 9, wherein the prongs are sized to engage and stabilize the predetermined area of the heart of the patient and are oriented generally parallel to each other.

11. The apparatus of claim 9, wherein the prongs each include a plurality of openings therein.

12. The apparatus of claim 9, wherein a portion of the second section of the bifurcated member is pivotally connected to the handle segment.

13. The apparatus of claim 9, wherein the second end portion of the handle segment is connected to a rib spreader.

14. The apparatus of claim 9, wherein the bifurcated member is rotatable with respect to the handle segment.

15. The apparatus of claim 9, wherein a plurality of elongated openings are located on the bifurcated member and the elongated openings form an elongate slot in each of the prongs.

16. The apparatus of claim 9, wherein the prongs of the bifurcated member are each movable relative to each other in response to movement of the first member.

* * * * *

UNITED STATES PATENT AND TRADEMARK OFFICE
CERTIFICATE OF CORRECTION

PATENT NO.     : 6,152,874
DATED          : November 28, 2000
INVENTOR(S)    : Christopher S. Looney, Gregory R. Furnish, and Michael W. Hipps It is certified that error appears in the above-identified patent and that said Letters Patent is hereby corrected as shown below:

Column 8, line 39, replace a "rib spreader 12, it is desired" with --a rib spreader, it is desired--.

Signed and Sealed this

Fifth Day of June, 2001

Attest:

*Attesting Officer*

NICHOLAS P. GODICI
*Acting Director of the United States Patent and Trademark Office*